(12) United States Patent
Saveliev et al.

(10) Patent No.: US 7,094,210 B2
(45) Date of Patent: Aug. 22, 2006

(54) METHOD OF WAVE BIOMECHANOTHERAPY

(76) Inventors: Boris Sergeevich Saveliev, Stroiteley 47-20 RU-455004, Magnitogorsk (RU); Vladimir Sergeevich Saveliev, Chernorechenskaya 42A-64 RU-443013, Samara (RU); Wladimir Wasilievich Skovorodnikov, Zvjozny gorodok 46-70 RU-141060, Moskowskaya obl. (RU); Wladlen Ivanovich Zinkovich, Zhukova 34-15 RU-445031, Tolyatti (RU); Nikolay Nikolaevich Golev, Leninsky prospekt 40-465 RU-445000, Tolyatti (RU)

( * ) Notice: Subject to any disclaimer, the term of this patent is extended or adjusted under 35 U.S.C. 154(b) by 529 days.

(21) Appl. No.: 10/623,184

(22) Filed: Jul. 18, 2003

(65) Prior Publication Data

US 2004/0097841 A1    May 20, 2004

(30) Foreign Application Priority Data

Jan. 24, 2001  (RU) .............................. 2001102239
Jan. 23, 2002  (WO) .................... PCT/RU02/00057

(51) Int. Cl.
  *A61H 23/02*    (2006.01)
  *A61N 5/067*    (2006.01)
  *A61F 7/00*     (2006.01)
(52) U.S. Cl. ............................. 601/15; 601/1; 601/46; 607/88; 607/96
(58) Field of Classification Search ............... None
  See application file for complete search history.

(56) References Cited

U.S. PATENT DOCUMENTS

| 4,231,355 | A |   | 11/1980 | Hara |  |
|---|---|---|---|---|---|
| 4,573,465 | A | * | 3/1986 | Sugiyama et al. | 606/11 |
| 5,336,159 | A | * | 8/1994 | Cheng | 601/15 |
| 5,746,702 | A |   | 5/1998 | Gelfgat et al. |  |
| 6,443,915 | B1 | * | 9/2002 | Hwang | 601/15 |
| 6,443,978 | B1 | * | 9/2002 | Zharov | 607/91 |
| 6,645,229 | B1 | * | 11/2003 | Matsumura et al. | 607/1 |
| 2003/0004556 | A1 | * | 1/2003 | McDaniel | 607/88 |
| 2004/0093047 | A1 | * | 5/2004 | Lach | 607/89 |

FOREIGN PATENT DOCUMENTS

| DE | 39 05 517 | 3/1990 |
|---|---|---|
| RU | 1795889 | 2/1993 |
| SU | 604211 | 11/1978 |
| WO | WO 00/67693 | 11/2000 |

* cited by examiner

*Primary Examiner*—Danton DeMille
(74) *Attorney, Agent, or Firm*—Pauley Petersen & Erickson

(57) ABSTRACT

For medicine, sports and cosmonautics, a method of biomechanotherapy massage and therapeutic action on a human body performed both by heat and light waves and by mechanical waves which are sequential and parallel combinations of longitudinal and transverse modulated solitary waves of length from 0.005 to 0.1 m propagating along the body with speed from 0.01 to 12 m/s, where the solitary waves are formed on the body due to an impulsive action of separate thermovibratodes interconnected with a controlled link and acting on a human body with a temperature from 0 to 90° C., a specific pressure from $0.5·10^5$ to $4·10^5$ Pa and a shear thrust from 0.1 to 100 N. The proposed method of biomechanotherapy allows to increase efficiency of the therapeutic and sports massage and to improve results of an integral treatment of various diseases. Wave biomechanotherapy increases 1.5–2 times the peripheral blood flow facilitating the work of the cardiovascular system, improving the rheological properties of blood, blood supply to all organs and the functional condition of these parameters. Wave biomechanotherapy actively stimulates the metabolism, accelerates rehabilitation processes in organs and tissues and increases drainage of decay products from a body in a natural way.

4 Claims, 3 Drawing Sheets

METHOD OF WAVE BIOMECHANOTHERAPY

BACKGROUND OF THE INVENTION

1. Field of the Invention

This invention relates to physical culture and sports, medicine, cosmonautics and can be used both for health-improving and therapeutic massage as well as for treatment of various diseases.

2. Discussion of Prior Art

U.S. Pat. No. 4,231,355 teaches a known method of pneumatic massage using shells and a harmonic progressing wave. This method provides an action of only a transverse mechanical wave propagating along a straight line, which does not agree with most of massage techniques performed by way of a curved path conditioned by, for example, blood and lymph flow of the massaged body part.

U.S.S.R. Inventor's Certificate 1795889 teaches a therapeutic massage using a progressing wave. This device produces only transverse mechanical waves propagating along a straight line on a limited number of anatomico-topographic body parts. Absence of heat waves, light waves, rarefaction waves, impulse displacement of pseudoboiling layer modules does not allow to effectively influence the lymph and blood flow. The known device cannot produce a modulated wave which is an important feature of a solitary wave due to use of modules of drivers to rotate discs. Starting, operation of the driver with the purpose to create chaotic motion of balls and shutdown of engines requires a significant amount of time, i.e. the process of a boiling layer production is inertial. In the "running wave" mode modules switch off for 5–10 sec, which corresponds to the wave propagation speed commensurable with a lymph flow velocity.

PCT International Publication WO/67693 teaches a method of massage that realizes only a mechanical progressing wave along the body in a lying position. To produce waves, four vibrators are used which are not positioned on one biomechanical unit, i.e. the wave length is significantly more than 0.1 m. Heat and light waves are absent. Mechanical impulse modulation parameters are the same for all vibration sources. Absence of a controlled connection between the vibratodes and large wave length do not allow a circular massage ensuring a body part clasping with force both stimulating blood flow and completely stopping it for a short period of time. Carrier frequency with this method does not correspond to the biomechanical resonance (5–20 Hz) and consequently cannot influence directly the blood flow in muscles.

FRG Patent Reference 39 05 517 C1 teaches a dampening, heating, vibrating, electrifying and freshening massage ball roller that does not ensure combinative effect of all acting factors, i.e. sequence of effects of heat, vibration and lighting with various time intervals. The known device uses a vibration drive that like all electric drives has a long response time and on-off time ratio equals to 2. Thus there is no possibility to program each mechanical impulse and to perform modulation of mechanical impulses in body reception mode. The device does not allow performing a circular massage, to synchronize phases of mechanical, heat and light impulses.

U.S.S.R. Inventor's Certificate 604211 teaches a method of wave therapy using cylindrical shells placed parallel to each other and pressed to a human body. Wave-like displacement of surface due to alternate shells filling and blowing-off provides for massage at a plane harmonic progressing wave synchronized with a pulse wave speed in extremities.

Lack of shear thrusts in this massage method precludes a stroking technique required to regulate musculocutaneous tonus in the process of treatment. The wave-like displacement with action modes are the same for all body parts and produces a harmonic progressing wave in relation to which a fast body adaptation takes place decreasing activity of the neuromuscular system, aimed at body rehabilitation while mechanical impulses are acting. This leads to a short duration of the treatment procedure (15–30 min) and the only controlled parameter changing for which it is possible to avoid adaptation is the wave speed. Thus there is no possibility to control treatment mode in a wide range. Another drawback of this known method is the impossibility to act with a wave on vibroreceptors and wave biomechanical processes in myofibrils. Also, this known method does not realize vacuumization waves, i.e. the waves with pressure less than $1.01 \cdot 10^5$ Pa.

SUMMARY OF THE INVENTION

One object of this invention is to increase efficiency of biomechanotherapy by creating a biomechanotherapy method with various massage techniques through the combined action on the body of modulated waves (heat, light, mechanical waves). A combination of waves presumes simultaneous action of several types of waves and the combined action of heat, light and mechanical waves is used in therapy, sequentially with different time intervals.

This object is achieved with a biomechanotherapy method by therapeutic action through combining heat, light and mechanical waves which represent sequential and parallel combinations of longitudinal and transverse modulated solitary waves with a length from 0.005 to 0.1 m and propagating along the body with speed from 0.01 to 12 m/s, with the longitudinal solitary waves forming on the body, due to impulsive displacement of separate vibratodes along the body surface, transverse solitary waves at right angle to the body surface, and the vibratodes connected by a controlled link and acting on human body at a temperature from 0 to 90° C., specific pressure from $0.5 \cdot 10^5$ to $4 \cdot 10^5$ Pa, shear thrust from 0.1 to 100 N and duration from 1 min to 10 hours.

Modulating oscillations of a solitary wave are impulses with frequency from 0.004 to 1 Hz and on-off time ratio equaling to the number of vibratodes participating in wave formation, and carrier waves are a sequence of impulses with frequency from 1 to 40 Hz and on-off time ration from 1.1 to 6, in relation to which frequency modulation is performed, for example by a sinusoidal signal with modulation frequency varying from 0.004 to 1 Hz, and frequency deviation varying from 0.001 to 40 Hz. Each vibrator is equipped with a radiator connected with a fiber-optic light guide to an internal source of laser light intensity of which is synchronized in phase with oscillations of thermomechanical impulses and all sources together are used to create a laser light solitary wave on the body surface. Into all vibratodes air at temperature from 0 to 90° C. is injected.

The essence of the invention is in use of sequential and parallel combinations of waves in therapy. In conventional therapeutic massage there is a sequential method of information transfer, which includes a sequential performance of therapeutic massage techniques. Parallel in time performance of several massage techniques with a manual massage is limited by physical abilities of a masseur, i.e. not more than two, and with an apparatus massage using the known devices is not provided. With the parallel combination of waves it is possible to perform massage of the entire body surface with simultaneous stimulation of arterial blood flow on some body parts and either lymph flow or venous outflow on other parts. In the proposed biomechanotherapy method a significant number of massage techniques performed in parallel (wave types) can be applied on one body part. Modulated solitary wave used in the proposed invention is a wave motion that at each moment of time is localized in finite region of space and in virtue of modulation changes its structure (amplitude, phase, frequency) during propagation. Thermovibratodes pressed against a human body, due to impulsive travel at right angle to a human body create a transverse wave and due to impulsive travel along the human body create a longitudinal wave. Thermal action during a vibratode filling creates a condition for penetration of heat into deeply located human tissues. Alternate heating of massaged body parts causes a heat wave propagating along the body surface. Impulse through-skin raying of blood causes a light wave with penetration depth depending on the vibratode pressure acting on a body and illumination intensity, and alternate raying of different body parts creates a light wave propagating along the body surface. With the fact that mechanical impulses parameters of different thermovibratodes differ and are set to create a wave travel of a solitary wave type, an occurring progressing wave acts as a particle and its energy is realized in a massage technique during travel. The wave length is determined depending on a massaged body part, used massage technique and geometrical dimensions of vibratodes. It was found that the wave travel can be realized effectively if on a biomechanical unit not less than four fixed vibratodes are used or one traveling vibratode. With a growing number of vibratodes massage efficiency increases. Maximum possible wave length depends on a pneumatic shell size used as a vibratode. It was noted that massage of a trunk as the biggest biomechanical human unit maximum diameter of the shell must be not more than 0.1 m. Similar surveys relating to massage of face muscles having minimal size showed that optimal size of a vibratode equals to 0.005 m. Thus the solitary wave length was taken from 0.005 to 0.1 m.

Wave propagation speed was determined based on the following. It is known that the average lymph movement speed is 0.01 m/s, and linear speed of blood flow in arteries is 0.4 m/s, in arterioles is 0.2 m/s, in capillaries is 0.05 m/s, in venules is 0.1 m/s, and in veins is 0.2 m/s. The speed of excitation transfer from pressure receptors along the postganglionic fibers of the vegetative nervous system equals 0.5–2 m/s. Speed of excitation transfer along other nervous fibers is from 3 to 120 m/s. The minimum speed of a solitary wave was selected to be equal to the lymph movement speed (0.01 m/s). Maximum speed was determined based on a task to stimulate blood flow in different sections of bloodstream, speed of excitation transfer from pressure receptors and speed of biomechanical wave processes in myofibrils. As for the level of action on blood flow and pressure receptors then for this wave speed of 2 m/s is sufficient. With regard to stimulation of wave processes in myofibrils this is not sufficient. Therefore, the following calculation was carried out. Solitary wave speed without a frequency modulation equals to:

$$V = d/T_H, \text{ but } f = 1/(q \cdot T_H), T_H = 1/(q \cdot f), \text{ hence } V = qdf,$$

where d is the linear dimension of a shell in the direction of wave propagation, $T_H$ is the shell filling time, q is the on-off time ration of mechanical impulses, and f is the frequency of vibroaction on muscles when shell filling time equals to blowing off time (at q=2).

Through experiments it was found that vibratory massage of muscles with frequency up to 40 Hz and on-off time ratio from 1.1 to 6 stimulates rehabilitation processes in muscles. It was possible to realize vibration with frequency of 40 Hz using a shell of d=0.05 m. Thus, maximum wave speed is equal to 12 m/s and is determined from the following relation:

$$V\max = q\max \, d\max \, f\max = 6 \cdot 0.05 \cdot 40 = 12 \text{ m/s}.$$

Such speed of elastic medium travel allows synchronizing the wave massage with speed of pulse wave in muscle-type vessels.

Presence in the proposed massage method of a great number of possible solitary wave travel directions (along the lymph flow, blood flow, neuroreflex channels and ways of muscle force propagation, i.e. along muscle fibers) allows to select required direction and with wave parameters to stimulate any particular physiological mechanism. Predominant direction of wave propagation is along the biomechanical meridians, lines on the body surface that are projections of muscles participating in motions and forming a waveguide system in which muscle force propagates ensuring biomechanical flow of lymph and blood. Performing a wave massage of the proposed technique along the biomechanical meridians allows to use massage techniques done with a curved path or simultaneously in several directions of a complex configuration and of long duration comparable with human body length or in opposite directions. For example, when a wave with speed of 0.01 m/s, stimulating a lymph flow and moving from the distal to proximal body part, is replaced with a wave of the opposite direction to stimulate arterial blood flow at speed of 8 m/s, it cannot be achieved with any type of apparatus massage including a manual massage.

Lower interval of thermal action equaling to 0° C. allows in the process of vibration with high on-off time ratio to achieve high speed of a body part cooling without a total human body temperature drop. Upper interval of thermal action equaling 90° C. allows in the process of vibration with the frequency of biomechanical resonance and high on-off time ratio to heat a body part without any burning injury and without total body temperature growth.

Action of an individual vibratode on the human body depends on an internal mechanical impulse and is determined by dynamics of adjacent vibratodes and forces between them, as well as controlling force moving vibratodes. Control over links between vibrators allows realizing shear forces in a massage required for example to apply a stroking technique. Measurements of masseur's force during massage as well as surveys to determine optimal vibratode force of action on a human body in the proposed method revealed specific pressure intervals. Maximum specific pressure is equal to $4 \cdot 10^5$ Pa and corresponds to the excess of $3.0 \cdot 10^5$ Pa over atmospheric pressure and is determined using a restorative (sports) massage procedure realizing greater force massage techniques than in cosmetic or therapeutic massage. Minimum specific pressure was determined based on the condition of efficiency of vacuumization wave measured by the level of blood inflow into massaged body part. As a result of the surveys it was discovered that no traumatizing of muscles occurred if minimum pressure equaled to $0.5 \cdot 10^5$ Pa and frequency of mechanical impulses was more than 1 Hz.

It is known that shear thrusts depend on the product of the force perpendicular to the surface by the friction factor, which is controlled by selection of elastic medium pressed against a body. In this invention the friction factor varies from 0.05 to 0.45 and averages to 0.25. Minimum shear force is determined based on the face massage conditions with normal force equaling to 0.4 N:

$f$ min shear=0.25·0.4=0.1 $N$.

With wave-like massage of a trunk normal maximum pressure may amount to 400N. Maximum shear thrust at that equals to:

$f$ max shear=0.25·400=100 $N$.

A modulated solitary wave may be considered as a group soliton (solitary wave), a wave train or a sequence of mechanical impulses propagating along a human body with a group velocity. During wave propagation in a train (package) change of amplitude and mechanical impulses frequency occurs, i.e. amplitude and frequency modulation of oscillations is observed. It is known that with any conventional oscillations modulation method the rate of amplitude and frequency change must be sufficiently low so that the modulated parameter cannot change almost during an oscillation period. In the method of this invention, this assumption is not used which allows to perform massage in the mode of environment reception by a body. Modulating oscillation parameters were determined in the following way. Modulating oscillation frequency is equal to:

$f=1/(N·T_B)$, with on-off time ratio of a modulating signal (relation of wave propagation time along all vibratodes to one vibratode oscillation time) equaling to:

$q=(N·T_B)/T_B=N$, where N is the number of vibratodes,
$T_B$ is the vibratode oscillation time.

The number of vibratodes for creation of a wave within the entire length of a biomechanical unit should be not less than 4 and as a rule not more than 32. Vibration duration with which no adaptation of a body to mechanical oscillations occurs equals to 8 sec. Then:

$f$ min=1/($N$ max·$T_B$ max)=/(32·0.8)=0.004 $Hz$.

$f$ max=1/($N$ min·$T_B$ min)=1/(4·0.25)=1 $Hz$.

The on-off time ratio varies from 4 to 32, and in a general case equals to the number of vibrators participating in a wave formation. The solitary wave carrier oscillations facilitate blood supply during a massage if presented by a sequence of mechanical impulses with frequency from 1 to 40 Hz and on-off time ratio from 1.1 to 6. In the method of this invention, a modulating signal has a shape of an impulse and the resultant is a train of oscillations in relation to which a frequency modulation is performed with a signal of any form including a sinusoidal signal. The oscillation frequency changes are per the following law:

$f=f_0+f\partial·\sin(2·q·v·t)$, where f is the oscillation frequency, Hz,
$f_0$ is the frequency at the initial moment of time, Hz,
$f\partial$ is the frequency deviation, Hz,
v is the modulation frequency, Hz, and
t is time.

Taking into account the fact that in the proposed method the frequency change rate is taken away, then the frequency deviation may have a value in the entire range of possible frequencies, i.e. from 0.001 to 40 Hz, and the modulation frequency corresponds to the frequency range of a modulating oscillation, i.e. 0.004–1 Hz. The lower frequency deviation value equaling to 0.001 is determined by the absence of physiological effects relating to frequency deviation below 0.001. Such approach excludes a fast adaptation of the body physiological indicators to biomechanotherapy techniques and allows performance of a massage both with one wave of 1 min duration and complete massage of 10 hours duration. A massage of less than 1 min duration does not cause any physiological shifts in a body. Significant duration of biomechanotherapy is of primary importance to restore an exercise performance of qualified sportsmen and to prevent postoperative complications and for cosmonauts to be able to work under weightlessness conditions. Studies showed that a biomechanotherapy of 10 hours duration allows sportsmen to restore physical abilities to a great extent after heavy physical activities, and allows patients to avoid a postanesthetic depression and bronchopulmonary complications accompanying a postoperative period.

BRIEF DESCRIPTION OF THE DRAWINGS

The proposed method of biomechanotherapy is illustrated with drawings.

DESCRIPTION OF PREFERRED EMBODIMENTS

Figure 1:
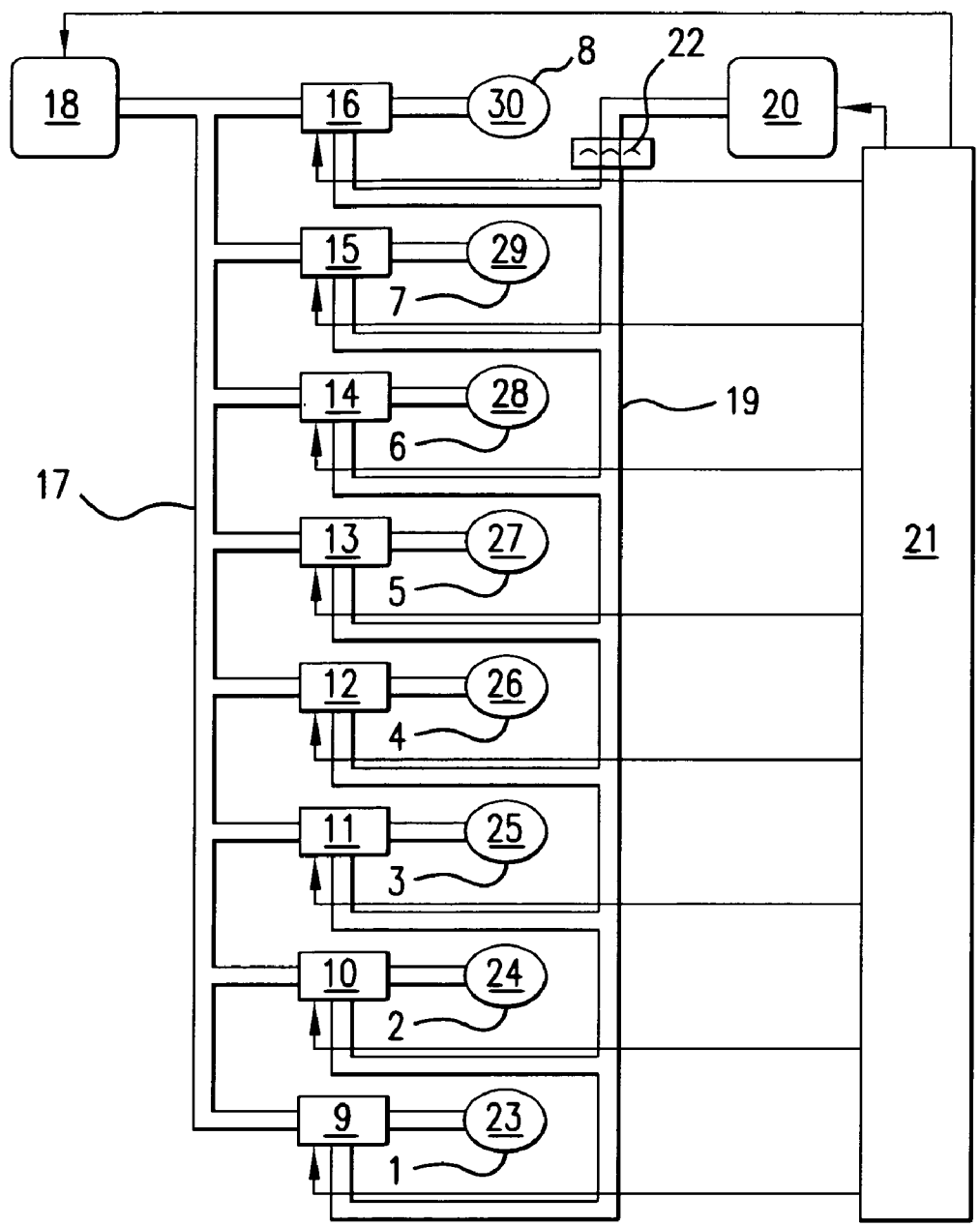
FIG. 1 shows the electropneumatic diagram of the device used to implement the proposed method with 8 vibratodes.

Electropneumatic system for implementation of the proposed method of biomechanotherapy (FIG. 1) includes vibratodes 1–8, working cavities of which are connected to air ducts with relevant three-line pneumatic valves 9–16, which communicate using air duct 17 with controlled source of vacuum 18 and using air duct 19 with controlled source of compressed air 20. Electromagnetic pneumatic valves and maintenance of pressure and vacuum are controlled by PC 21. To heat or cool the air supplied to vibratodes, conditioner 22 is used. Software-based control of valves is carried out by the input of an electrical signal to the valve winding. Working cavity of a vibratode is connected to the compressed air source, and in the case of absence of electric current in the valve winding, the working cavity will be connected to either the vacuum source or to the atmosphere. All vibratodes are also equipped with laser light sources 23–30.

Figure 2:
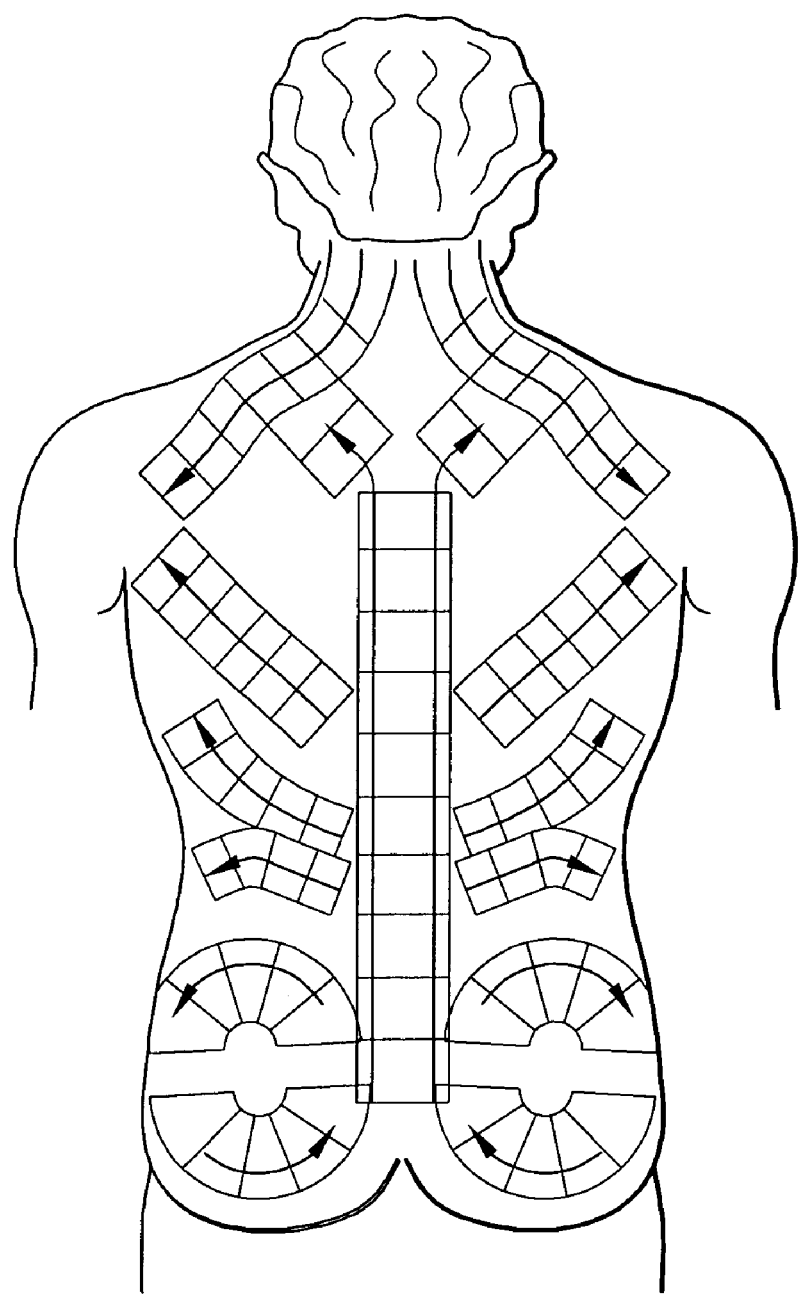
FIG. 2 shows vibratodes layout during therapeutic massage of back muscles.
Figure 3:
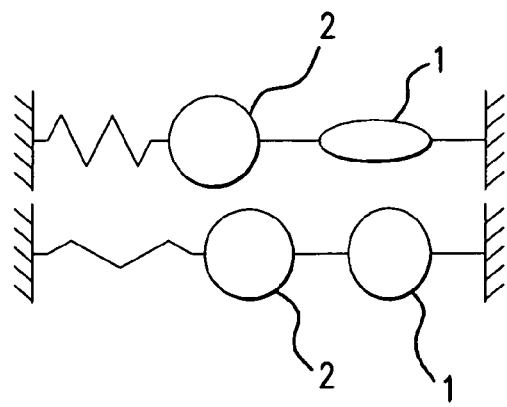
FIG. 3 shows regulation diagram for elastic links between vibratodes.
Figure 4:
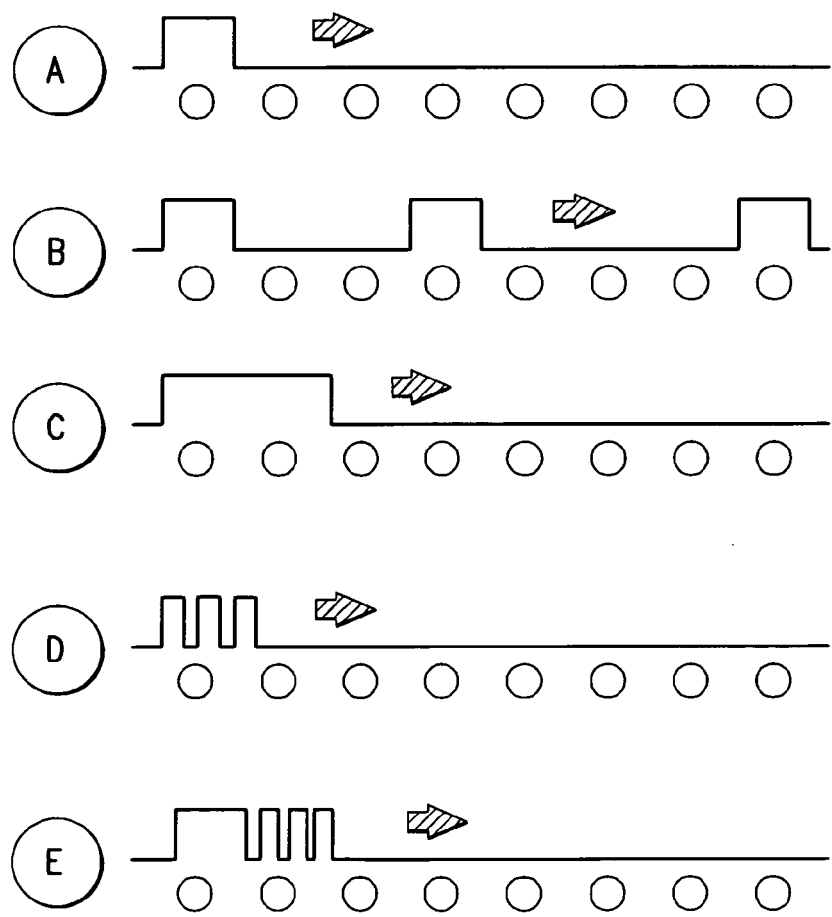
FIG. 4 shows wave types used in the proposed method.

Using the device shown in FIG. 1 the biomechanotherapy method is implemented in the following way. Consider the example of back muscles biomechanotherapy that can be realized by use of vibratodes located on a human body as shown in FIG. 2. Each vibratode rotation axis is perpendicular to the biomechanical meridian. If the wave in the method of this invention of biomechanotherapy moves continuously, then the biomechanical meridian often corresponds to directions of main massage motions in a manual massage. To regulate the elastic link some shells are of significantly smaller size than the massage ones and when filled not only act on a human body but also perform the function of a rubber drive moving adjacent vibratodes. Elastic link regulation design is shown in FIG. 3. When shell 31 is filled (FIG. 3) massage vibratode 32 moves, i.e. shear thrusts appear. Using the described device several types of waves can be realized (FIG. 4):

- A—waves formed by action of single impulses of 1–8 vibratodes,
- B—waves formed by action of single impulses with spacing of 1–3 vibratodes from each other,
- C—waves of two duplex mechanical impulses,
- D—waves formed by action of separate vibratodes in the form of mechanical impulses sequence, and
- E—waves of two duplex impulses, the second one filled with high frequency carrier oscillations.

Depending on the vibratode location mechanical impulses frequency is selected. Naturally in the process of a wave-like travel frequency varies from vibratode to vibratode. If there is a wave of single impulses then the frequency modulation manifests itself in the wave speed variation while moving from vibratode to vibratode.

Consider the example of the method of biomechanotherapy of back muscles (thoracic part of spinal cord). Stroking and petrissage are used as the main massage techniques. The study revealed that stroking corresponds to waves A05, B05, C05, E05 with speed of 0.5 m/s. Petrissage corresponds to wave C0166 formed by duplex impulses with speed of 0.166 m/s. Petrissage also corresponds to waves D0125 propagating with speed of 0.125 m/s, frequency 5 Hz and on-off time ratio of 2, vibration time on each vibratode 4 sec, modulation frequency of 0.5 Hz, frequency deviation of 20 Hz. The massage is performed per scheme A05, A05, C05, E05, A05, C0166, A05, D0125, A05, C05, A05, which means the order of wave actions. It should be noted that in the process of biomechanotherapy any therapeutic massage session as a rule is followed by the stroking technique using wave A05. The thermal regulation of vibratodes is carried out by supply of air of different temperatures and serves as a thermobiomechanical toning up of muscles. Vibratodes can either include sources of laser light or can be made of a transparent elastic shell with an outside radiator connected by a fiber optic light guide to an internal laser light source with the illumination intensity synchronized in phase with mechanical impulses oscillations, and all sources in total are used for a solitary light wave creation. Wave travel of separate vibratodes can not only apply pressure but also cause vacuumization waves. Vacuumization in a separate vibratode and pressure in adjacent vibratodes form a vacuumization zone on a body. With the vacuumization zone moving a vacuumization wave if formed on a human body.

It is known that blood flow velocity depends on the body temperature. It was noted that temperature increase during physical work facilitates hemodynamics increase. To enhance efficiency of biomechanotherapy air supplied to the vibratodes is heated. The highest heat transfer from the massage vibrator to the human body occurs at the moment of filling. Thus, thermal waves are formed on a human body causing a temperature drop in massaged muscles and as a result thermobiomechanical toning up of muscles. This results in the improvement of the contractile muscle function through thermostimulating of a body synchronously with vibrations of muscles being in the biomechanical resonance mode. Presence of a radiator in a vibratode allows performing a through-skin raying of blood, to act noninvasively with electromagnetic radiation on reflexogenic zones and biologically active spots in the process of a wave biomechanotherapy. Phase synchronization of mechanical oscillations of vibratodes and radiation intensity allow increasing efficiency of the biological stimulation of vital function of a body in total. This is conditioned by the synchronization of macro- (massage) and micro- (radiation) actions.

EXAMPLE 1

Patient T., 42 years old, underwent a treatment at the Regional clinical hospital from 28 Jul. 2000 to 20 Sept. 2000. After the complete integral checkup the clinical diagnosis resulted in disseminated osteochondrosis of the lumbar part of spinal cord with a marked radicular syndrome. To perform a session of the biomechanotherapy the patient took the horizontal position. Beneath the patient's back a massage device (a rug) with vibratodes of different diameters was placed. 10 sessions were prescribed for the treatment course. During five initial procedures therapeutic action mode was used, during the last five procedures, sports mode (more intensive) was used. Condition of the patient after completion of the wave biomechanical action course improved significantly. Pain syndrome in the area of affected vertebrae practically completely stopped and movement function of the spine was significantly restored. There were no complications, pains or unpleasant feelings during the procedures. In conclusion, wave biomechanotherapy is a sufficient enough method of action in a complex treatment of patients suffering from a disseminated osteochondrosis. This method becomes important during treatment of patients suffering from a polyvalent allergy to medicines or with contra-indications for physiotherapeutic treatments, in particular for manual therapy.

EXAMPLE 2

Patient M., 59 years old, underwent treatment at the Phlebology Department of the Hospital Surgery Clinic from 18.09.2000 to 02.10.2000. After the complete integral checkup the clinical diagnosis resulted in a condition after the right-side radical mastectomy in 1991 and there was secondary lymphostasis of the upper right extremity of stage m. During examination a significant enlargement of the upper right extremity was observed and at the level of the wrist joint circumference amounted to 35.5 cm, at the upper third of the forearm was 37 cm, at the medium third of the upper arm was 37 cm. During the biomechanotherapy session a special cuff for an upper extremity containing vibratodes was placed in the area from the middle of the hand back with direction of a massage wave movement from fingers. The cuff was applied with a possible maximum pressure to the body. For the biomechanotherapy session it is recommended to apply an elastic bandage on an extremity. The upper extremity was placed in the lifted position as the most physiological for this procedure. 10 sessions were prescribed for the treatment course. During the initial 7 procedures the therapeutic action mode was used, during the last 3 procedures the sports mode was used. Patient's condition after the wave biomechanotherapy course improved, the extremity edema noticeably decreased, and the condition of the coverlet improved. Circumference at the level of the wrist joint became 29.5 cm, at the upper third of the forearm was 33.5 cm, at the medium third of the upper arm was 33 cm. There were no complications, pains or unpleasant feelings during the procedures. In conclusion, wave biomechanotherapy is a sufficient enough method of action in a complex treatment of patients suffering from a secondary lymphostasis of extremities, as well as for a preoperative preparation and postoperative rehabilitation of this category of patients.

The proposed method of biomechanotherapy allows to increase efficiency of the therapeutic and sports massage and to improve results of an integral treatment of various diseases. Wave biomechanotherapy provides an action in the range the muscle biomechanical resonance frequencies, from 5 to 20 Hz creating optimal conditions for a full-fledged restoration of the neuromuscular system. Working based on the principal of a solitary progressing wave, the wave biomechanotherapy using the proposed method increases 1.5–2 times the peripheral blood flow facilitating the work of the cardiovascular system, improving the rheological properties of blood, blood supply to all organs and functional condition of these parameters. Actively stimulating the metabolism, the wave biomechanotherapy accelerates rehabilitation processes in cells and tissues and increases drainage of decay products from a body in a natural way. Use of the wave biomechanotherapy results in the improvement of the general state of health and vigor, in the growth of the exercise performance, in the increase of the muscles elasticity and the ligamentous apparatus mobility, in the elimination of the congestion and edema phenomena. It is important that the above listed results are achieved using the internal body resources avoiding artificial stimulators, medicines and exhausting exercising. This invention can arrive at the most extensive application in medicine, sports, and cosmonautics.

We claim:

1. A method of wave biomechanotherapy using waves formed by a wave-type travel of an elastic medium pressed against a human body, the method comprising the steps of: performing a therapy with a combination of heat, light and mechanical waves which are sequential and parallel combinations of longitudinal and transverse modulated solitary waves having a length from 0.005 m to 0.1 m propagating along the human body with a speed from 0.01 m/s to 12 m/s, forming the longitudinal solitary waves on the human body as an impulsive travel of separate vibratodes along a body surface, forming the transverse solitary waves on the human body as an impulsive travel of separate vibratodes at a right angle to the body surface, and interconnecting the vibratodes with a controlled link and acting on the human body with a temperature from 0° C. to 90° C., a specific pressure from $0.5 \cdot 10^5$ to $4 \cdot 10^5$ Pa, a shear thrust from 0.1 to 100 N, and a duration from 1 mm to 10 hours.

2. The method of wave biomechanotherapy according to claim 1, wherein modulating oscillations of a solitary wave are impulses with frequency from 0.004 Hz to 1 Hz, an on-off time ratio equal to a number of vibratodes participating in a waves formation and carrier oscillations are a sequence of impulses with a frequency from 1 Hz to 40 Hz and an on-off time ratio from 1.1 to 6, in relation to which a frequency modulation is performed, including by a sinusoidal signal with the frequency modulation varying from 0.004 Hz to 1 Hz and a frequency deviation varying from 0.001 Hz to 40 Hz.

3. The method of wave biomechanotherapy according to claim 1, wherein each vibratode has with a radiator connected with a fiber optic light guide to an internal laser light source with an illumination intensity synchronized in phase with thermomechanical impulses oscillations, and all sources in total are used to create a laser light solitary wave on the body surface.

4. The method of wave biomechanotherapy according to claim 1, wherein therapy air of a temperature from 0° C. to 90° C. is supplied into the vibratodes.

* * * * *